(12) United States Patent
Clary et al.

(10) Patent No.: US 11,518,767 B2
(45) Date of Patent: Dec. 6, 2022

(54) MTOR INHIBITOR COMPOUNDS

(71) Applicant: GALDERMA RESEARCH & DEVELOPMENT, Biot (FR)

(72) Inventors: Laurence Clary, La Colle sur Loup (FR); Jean-François Fournier, Antibes (FR); Gilles Ouvry, Biot (FR); Yushma Bhurruth-Alcor, Ashburn, VA (US); Etienne Thoreau, Saint Vallier de Thiey (FR); Loïc Tomas, La-Tour-de-Peilz (CH)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 16/907,122

(22) Filed: Jun. 19, 2020

(65) Prior Publication Data

US 2020/0317683 A1 Oct. 8, 2020

Related U.S. Application Data

(63) Continuation of application No. PCT/EP2018/086074, filed on Dec. 20, 2018.

(30) Foreign Application Priority Data

Dec. 21, 2017 (FR) ...................... 1771402

(51) Int. Cl.
| | |
|---|---|
| *C07D 487/20* | (2006.01) |
| *C07D 487/04* | (2006.01) |
| *A61P 17/00* | (2006.01) |
| *A61P 17/06* | (2006.01) |
| *A61P 35/00* | (2006.01) |
| *A61P 17/10* | (2006.01) |
| *A61K 9/00* | (2006.01) |
| *A61K 31/519* | (2006.01) |

(52) U.S. Cl.
CPC .......... *C07D 487/20* (2013.01); *A61K 9/0014* (2013.01); *A61P 17/00* (2018.01); *A61P 17/06* (2018.01); *A61P 17/10* (2018.01); *A61P 35/00* (2018.01); *C07D 487/04* (2013.01)

(58) Field of Classification Search
CPC .............................. C07D 487/04; C07D 487/20
See application file for complete search history.

(56) References Cited

U.S. PATENT DOCUMENTS

2016/0038497 A1  2/2016  Liu et al.

FOREIGN PATENT DOCUMENTS

| EP | 2 705 181 B1 | 3/2014 |
|---|---|---|
| WO | WO-2005/028434 A2 | 3/2005 |
| WO | WO-2007/061737 A2 | 5/2007 |
| WO | WO-2009/062118 A2 | 5/2009 |
| WO | WO-2009/117482 | 9/2009 |
| WO | WO-2012/148540 A1 | 11/2012 |
| WO | WO-2012/154695 A2 | 11/2012 |
| WO | WO-2015/074135 A1 | 5/2015 |
| WO | WO-2019/122059 A1 | 6/2019 |

OTHER PUBLICATIONS

Buerger, Claudia, et al., "Blocking mTOR Signalling with Rapamycin Ameliorates Imiquimod-induced Psoriasis in Mice," Journal Compliation, Acta Dermato-Venereologica 2017; 97: 1087-1094, doi: 10.2340/00015555-2724.
International Search Report dated Mar. 11, 2019 received in corresponding International Application No. PCT/EP2018/086066 (2 pages).
International Search Report dated Mar. 27, 2019 received in corresponding International Application No. PCT/EP2018/086074 (3 pages).
Hackam et al., "Translation of Research Evidence From Animals to Humans", JAMA, 296(14), 2006, pp. 1731-1732 (5 pages).
Jordan, "Tamoxifen: A Most Unlikely Pioneering Medicine", Nature Reviews, vol. 2, 2003 (9 pages).

*Primary Examiner* — Susanna Moore
(74) *Attorney, Agent, or Firm* — Sunit Talapatra; Foley & Lardner LLP

(57) ABSTRACT

The invention relates to novel mTOR inhibitor compounds having the general formula (I), to compositions comprising said mTOR inhibitor compounds, methods for producing same, and the use thereof in compositions as a drug.

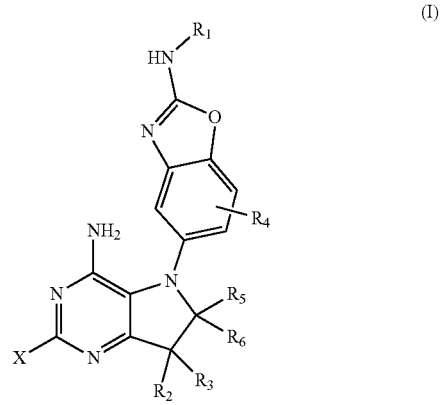

10 Claims, 2 Drawing Sheets

MTOR INHIBITOR COMPOUNDS

CROSS-REFERENCE TO RELATED APPLICATIONS

This application is a continuation of International Application No. PCT/EP2018/086074 filed Dec. 20, 2018, which claims the benefit of and priority to FR Application No. 1771402 filed Dec. 21, 2017, both of which are hereby incorporated by reference herein in their entireties.

FIELD OF INVENTION

The present invention relates to novel compounds which inhibit the serine/threonine kinase mTOR ("mechanistic target of rapamycin", also known as FRAP, RAFT, RAPT and SEP). The invention also relates to compositions comprising same, to processes for preparing same and to the uses thereof in compositions as medicament.

BACKGROUND OF THE INVENTION

The protein kinase mTOR is the catalytic center of two functionally distinct multiprotein complexes, conserved in all eukaryotes and named mTORC1 and mTORC2 (Dunlop et al., "Mammalian target of rapamycin complex 1: signalling inputs, substrates and feedback mechanisms", 2009; Guertin et al., "The pharmacology of mTOR inhibition", 2009). When it is associated with Raptor (regulatory associated protein of TOR) and with mLST8 (mammalian lethal with sec13 protein 8), mTOR forms the complex mTORC1. This complex interacts with Deptor (DEP domain-containing mTOR-interacting protein), FKBP38 and PRAS40 (proline-rich Akt substrate of 40 kDa), which are down-regulators of mTORC1. To form mTORC2, mTOR interacts with the proteins Rictor (rapamycin-insensitive companion of TOR), Sin1 (stress-activated map kinase-interacting protein 1) and mLST8. Furthermore, mTORC2 also becomes associated with Deptor, which represses its activity, and also with PPR5/Protor, the function of which remains unknown. When it is bound to FKBP12, rapamycin specifically inhibits mTORC1.

mTOR is notably known for regulating cell proliferation, cell growth, cell mobility, cell survival, protein biosynthesis and transcription.

It has been shown that disruptions of the mTOR signaling pathway are the cause of several diseases, in particular various types of cancer and multiple hamartomas.

Patent WO 2007/061737, which discloses mTOR-inhibiting bicyclic compounds, is known, for example. They are used in cancer treatment, such as breast cancer, lung cancer, non-small-cell lung cancer, kidney cancer, renal carcinoma, prostate cancer, blood cancer, liver cancer, ovarian cancer, thyroid cancer, endometrial cancer, lymphoma, renal cell carcinoma, or mantle cell lymphoma.

Patent WO 2009/117482 is also known, which more particularly describes salts and other polymorphs of mTOR-inhibiting bicyclic compounds, also used in cancer treatment, of the same type as those described in WO 2007/061737.

Rapamycin, an mTOR inhibitor, has been known for a long time for its immunosuppressant properties. It has, nevertheless, shown limited therapeutic success when it is administered systemically to patients suffering from psoriasis. Also, recent data have shown that the mTOR signaling pathway is hyperactivated in lesional psoriatic skin, which may contribute toward the disease by interfering with keratinocyte maturation. The effect of topical treatment with rapamycin in a model of imiquimod-induced psoriatic mice was studied (Burger et al., "Blocking mTOR Signalling with Rapamycin Ameliorates Imiquimod-induced Psoriasis in Mice", 2017). The immunohistological analysis revealed that rapamycin not only prevented activation of the mTOR signaling pathway (levels of P-mTOR and of P-S6), but almost normalized the expression of the epidermal differentiation markers. In addition, the influx of innate immune cells into the draining lymphatic ganglions was partially reduced by treatment with rapamycin. These data emphasize the role of the mTOR signaling pathway in the pathogenesis of psoriasis, and support the study of the topical inhibition of mTOR as a novel anti-psoriasis strategy.

SUMMARY OF THE INVENTION

There is thus a real need to develop treatments, in particular topical treatments, for patients suffering from diseases such as psoriasis.

Taking the foregoing into account, one problem that the invention proposes to solve is that of proposing novel mTOR inhibitors notably for improving the treatment of immune-mediated proliferative or inflammatory skin diseases.

The Applicant has developed novel mTOR-inhibiting compounds.

One aspect of the present invention is thus an mTOR-inhibiting compound of general formula (I)

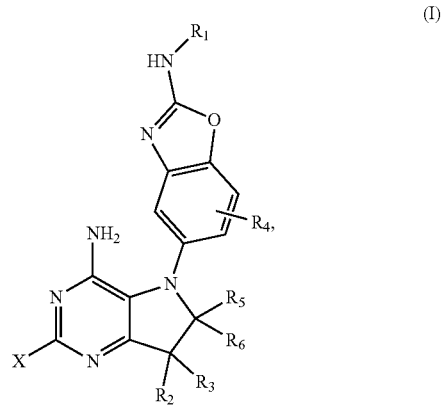

or a pharmaceutically acceptable salt thereof, in which each variable is as defined and described hereinbelow.

An aspect of the invention is also a composition comprising, in a physiologically acceptable medium, an mTOR-inhibiting compound of formula (I) according to the invention or a pharmaceutically acceptable salt thereof. It is intended to be used as a medicament, in particular in the treatment of diseases involving an mTOR enzyme with serine-threonine kinase activity and notably in the treatment of dermatological complaints associated with a keratinization disorder with a proliferative, inflammatory and/or immunoallergic component, for instance psoriasis, atopic dermatitis, actinic keratosis or acne, preferentially atopic dermatitis, more preferentially the inflammatory component of atopic dermatitis and even more preferentially topical treatment of the inflammatory component of atopic dermatitis.

BRIEF DESCRIPTION OF THE DRAWINGS

The invention will be better understood on reading the nonlimiting description which follows, which has been drafted with regard to the attached drawings, in which.

Figure 1:
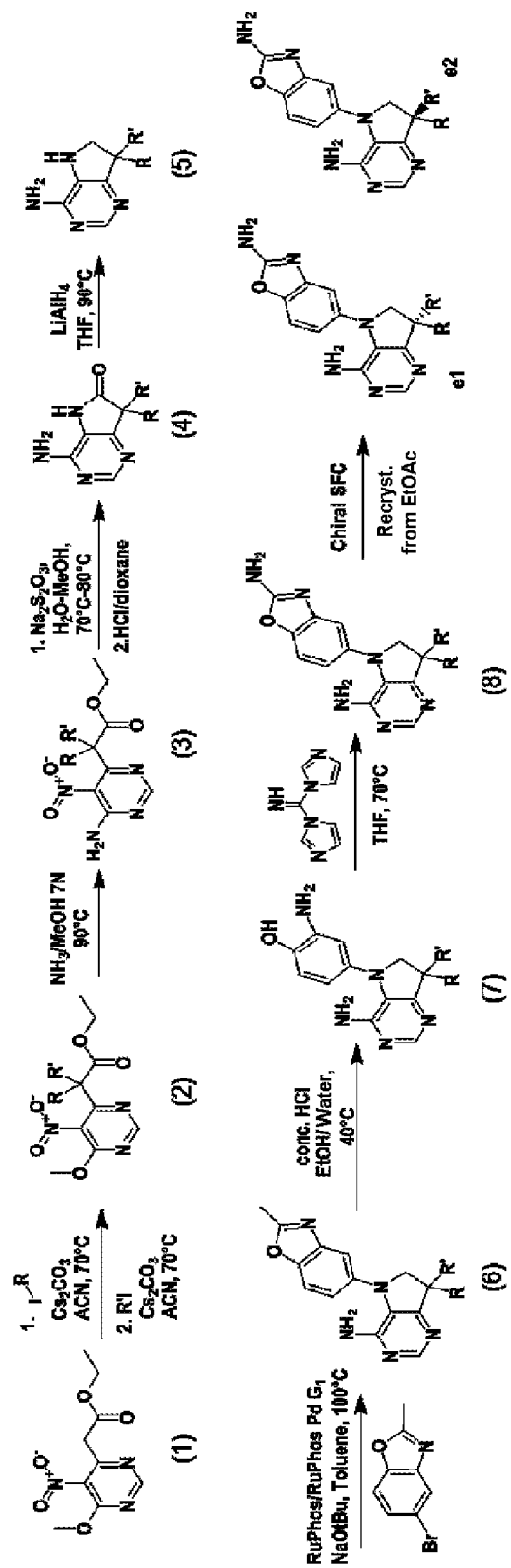
FIG. 1 represents a route for synthesizing the compounds 5-(4-amino-7-isobutyl-7-methyl-6,7-dihydro-5H-pyrrolo[3,2-d]-5-yl)benzo[d]oxazol-2-amine (enantiomer 1-e1) and 5-(4-amino-7-isobutyl-7-methyl-6,7-dihydro-5H-pyrrolo[3,2-d]pyrimidin-5-yl)benzo[d]oxazol-2-amine (enantiomer 2-e2)

The present invention relates to novel mTOR-inhibiting compounds or a pharmaceutically acceptable salt thereof.

The term "mTOR inhibitor" refers to compounds which down-regulate, i.e. reduce, block or even suppress, the activation of the mTOR signaling pathway, by competing, advantageously selectively, with the substrates at the level of mTORC1 and/or mTORC2 or by modifying the active site of these enzymes which can thus no longer catalyze a given substrate.

The compounds according to the invention may be represented by the general formula (I)

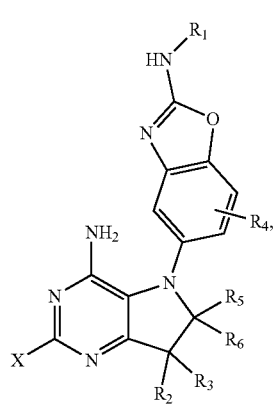

(I)

or a pharmaceutically acceptable salt thereof, in which:

$R_1$ represents a hydrogen atom or a $C_1$-$C_3$ alkyl, cyclopropyl or acyl radical;

$R_2$ and $R_3$ represent, independently of each other, a hydrogen atom, a halogen atom chosen from Cl and F, a linear or branched $C_1$-$C_6$ alkyl radical, optionally interrupted with a heteroatom O, S or —$NR_7$, and unsubstituted or substituted with a $C_3$-$C_5$ cycloalkyl or heterocycloalkyl or an aromatic ring/heterocycle which is unsubstituted or mono- or polysubstituted with a halogen atom chosen from Cl and F or an —OH, methyl (Me) or —OMe radical, or together form a $C_3$-$C_6$ ring or heterocycloalkyl;

it being understood that $R_2$ and $R_3$ do not both represent a halogen atom;

with $R_7$ representing a hydrogen atom or a $C_1$-$C_3$ alkyl, acyl or $C_1$-$C_4$ carboxyalkyl radical;

$R_4$ represents a hydrogen atom, a halogen atom chosen from F, Cl and Br, or a radical from among —$OR_8$, $C_1$-$C_3$ alkyl and cyclopropyl;

with $R_8$ representing a hydrogen atom or a $C_1$-$C_3$ alkyl, cyclopropyl or acyl radical;

$R_5$ and $R_6$ represent, independently of each other, a hydrogen atom, a $C_1$-$C_3$ alkyl or cyclopropyl radical, or together form a carbonyl or a $C_3$-$C_4$ ring; and X represents a hydrogen atom or an —$NH_2$, —OH or methyl radical.

According to the present invention, the term "alkyl" means a linear or branched radical containing, for example, from 1 to 6 ($C_1$-$C_6$) or from 1 to 3 ($C_1$-$C_3$) carbon atoms, advantageously methyl, ethyl, propyl, isopropyl, butyl, tert-butyl, 2-methylbutyl, pentyl, 2-methylpentyl or hexyl radicals.

The term "acyl" means a radical obtained by removing the hydroxyl group from a carboxylic acid; the acyl group corresponding to a carboxylic acid of formula —RCOOH will have the formula —RCO, in which the carbon atom and the oxygen atom are linked via a double bond (carbonyl group).

The term "cycloalkyl" means a cycloalkyl radical containing from 3 to 6 carbon atoms advantageously chosen from cyclopropyl, cyclopentyl and cyclohexyl.

The term "heterocycloalkyl" or "heterocycle" means, for example, a piperidino, morpholino, pyrrolidino or piperazino radical.

The term "aromatic ring" means a flat cyclic radical containing (4n+2) delocalized electrons, n being the number of rings constituting the radical; if the ring contains elements other than carbon and hydrogen, it is referred to as an aromatic heterocycle.

When the compounds according to the invention are in the form of a pharmaceutically acceptable salt, it is preferably a salt obtained from a nontoxic base or acid.

The term "pharmaceutically acceptable salt" refers to salts which are, in the context of good medical judgement, suitable for use in contact with human and lower animal tissues without excessive toxicity, irritation, allergic response and the like and are commensurate with a reasonable benefit/risk ratio. Pharmaceutically acceptable salts are well known in the prior art. The pharmaceutically acceptable salts of the compounds of the present invention comprise those derived from suitable inorganic and organic acids and bases.

When the compound of the present invention is acidic, its corresponding salt may be prepared from pharmaceutically acceptable nontoxic bases, comprising inorganic bases and organic bases.

The salts derived from these inorganic bases comprise aluminum, ammonium, calcium, copper, iron, lithium, magnesium, manganese, potassium, sodium and similar salts. The ammonium, calcium, magnesium, potassium and sodium salts are particularly preferred.

The salts derived from pharmaceutically acceptable nontoxic organic bases comprise salts of primary, secondary and tertiary amines, and also of cyclic amines and of substituted amines such as naturally substituted and synthesized amines.

Other pharmaceutically acceptable nontoxic organic bases from which salts may be formed comprise ion-exchange resins, for instance arginine, betaine, caffeine, choline, N',N'-dibenzylethylenediamine, diethylamine, 2-diethylaminoethanol, 2-dimethylaminoethanol, ethanolamine, N,N-diethylethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt may be prepared from pharmaceutically acceptable nontoxic acids, comprising inorganic acids and organic acids.

Such acids comprise, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric or p-toluenesulfonic acid and the like. Citric, hydrobromic, hydrochloric, maleic, phosphoric, sulfuric and tartaric acid are particularly preferred.

DESCRIPTION OF EMBODIMENTS

According to one embodiment of the invention, the pharmaceutically acceptable salt is chosen from tromethamine, sodium, calcium and L-arginine.

According to another embodiment of the invention, the salt is chosen from magnesium, potassium, N,N-diethylethanolamine, N-methyl-D-glucamine and piperazine.

In certain embodiments, the salt is in hydrate or solvate salt form.

In certain embodiments, the salt is substantially in amorphous form.

In certain embodiments, the salt is essentially in crystalline form.

In certain embodiments, the salt is crystalline to at least about 95% by weight.

In certain embodiments, the salt is substantially in single crystalline form.

According to the present invention, the preferred compounds of formula (I) or a pharmaceutically acceptable salt thereof are those in which:

$R_1$ represents a hydrogen atom;

$R_2$ and $R_3$ represent, independently of each other, a hydrogen atom, a linear or branched $C_1$-$C_4$ alkyl radical, optionally interrupted with a heteroatom S or —$NR_7$, or together form a Ca heterocycloalkyl;

with $R_7$ representing an acyl or carboxy-tert-butyl radical;

$R_4$ represents a hydrogen atom;

$R_5$ and $R_6$ represent, independently of each other, a hydrogen atom, a methyl group, or together form a carbonyl; and X represents a hydrogen atom.

More preferentially, the compounds of formula (I) or a pharmaceutically acceptable salt thereof are those in which:

$R_1$ represents a hydrogen atom;

$R_2$ represents a methyl group;

$R_3$ represents a linear or branched $C_1$-$C_4$ alkyl radical, for instance a methyl, ethyl, propyl, isopropyl, butyl, isobutyl or tert-butyl, optionally interrupted with an S heteroatom;

$R_4$ represents a hydrogen atom;

$R_5$ and $R_6$ represent a hydrogen atom; and

X represents a hydrogen atom.

Even more preferentially, the compounds of formula (I) or a pharmaceutically acceptable salt thereof are those in which:

$R_1$ represents a hydrogen atom;

$R_2$ represents a methyl group;

$R_3$ represents an isobutyl group, the two enantiomers R and S being represented, $R_4$ represents a hydrogen atom;

$R_5$ and $R_6$ represent a hydrogen atom; and

X represents a hydrogen atom.

Among the compounds of formula (I) which fall within the context of the present invention, mention may notably be made of the following compounds:

5-(4-Amino-7-isobutyl-7-methyl-6,7-dihydro-5H-pyrrolo[3,2-d]pyrimidin-5-yl)benzo[d]oxazol-2-amine (enantiomer 1);

5-(4-Amino-7-isobutyl-7-methyl-6,7-dihydro-5H-pyrrolo[3,2-d]pyrimidin-5-yl)benzo[d]oxazol-2-amine (enantiomer 2);

5-(2-Aminobenzoxazol-5-yl)-7-isobutyl-6,7-dihydro-5H-pyrrolo[3,2-d]pyrimidin-4-ylamine;

5-(2-Aminobenzoxazol-5-yl)-7-methyl-7-methylsulfanylmethyl-6,7-dihydro-5H-pyrrolo[3,2-d]pyrimidin-4-ylamine;

5-(4-Amino-7,7-diethyl-6,7-dihydro-5H-pyrrolo[3,2-d]pyrimidin-5-yl)benzo[d]oxazol-2-amine;

5-(2-Aminobenzoxazol-5-yl)-7,7-dimethyl-6,7-dihydro-5H-pyrrolo[3,2-d]pyrimidin-4-ylamine;

5-(2-Aminobenzoxazol-5-yl)-7-methyl-7-propyl-6,7-dihydro-5H-pyrrolo[3,2-d]pyrimidin-4-ylamine;

5-(2-Aminobenzoxazol-5-yl)-7,7-diethyl-6-methyl-6,7-dihydro-5H-pyrrolo[3,2-d]pyrimidin-4-ylamine;

4-Amino-5-(2-aminobenzoxazol-5-yl)-7,7-dimethyl-5,7-dihydro-pyrrolo[3,2-d]pyrimidin-6-one;

1-Acetyl-4'-amino-5'-(2-aminobenzo[d]oxazol-5-yl)spiro[azetidine-3,7'-pyrrolo[3,2-d]pyrimidin]-6'(5'H)-one;

tert-Butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate;

tert-Butyl 4'-amino-5'-(2-aminobenzo[d]oxazol-5-yl)-5',6'-dihydrospiro[azetidine-3,7'-pyrrolo[3,2-d]pyrimidine]-1-carboxylate.

An aspect of the present invention is also a composition comprising, in a physiologically acceptable medium, a compound of formula (I) according to the invention as defined above or a pharmaceutically acceptable salt thereof.

A pharmaceutically acceptable medium denotes a medium that is compatible with and suitable for use in contact with human and animal cells, in particular with the skin, mucous membranes and/or the integuments, without undue toxicity, irritation or allergic response or the like, and commensurate with a reasonable benefit/risk ratio.

A pharmaceutically acceptable medium according to the invention may comprise any known adjuvant used in the pharmaceutical field, which is compatible with the mTOR-inhibiting compounds according to the invention.

Nonlimiting examples that may be mentioned include solvents, buffers, aromatizing agents, binders, chelating agents, surfactants, thickeners, lubricants, gellants, humectants, moisturizers, preserving agents, antioxidants, calmative agents, pro-penetrating agents, colorants, fragrances and the like, or a mixture thereof.

Needless to say, a person skilled in the art will take care to select the optional compound(s) to be added to these compositions such that the advantageous properties intrinsically associated with the present invention are not, or are not substantially, adversely affected by the envisaged addition. Their concentration is also chosen so that they do not harm the advantageous properties of the compounds according to the invention.

The compound according to the present invention and the composition comprising same may be administered orally, rectally, topically or parenterally (subcutaneously, intramuscularly or intravenously). They are preferably administered orally or topically, more preferentially topically.

The compositions according to the invention may be in liquid, solid or gas form.

Via the oral route, the composition may be in the form of tablets, gel capsules, coated tablets, syrups, suspensions, solutions, powders, granules, emulsions, suspensions of microspheres or nanospheres or lipid or polymeric vesicles allowing controlled release.

Via the parenteral route, the composition may be in the form of solutions or suspensions for perfusion or for injection.

Preferably, the pharmaceutical composition is conditioned in a form that is suitable for topical application.

Via the topical route, the compositions, which are thus more particularly intended for treating the skin and mucous membranes, may be in liquid, pasty or solid form, and more particularly in the form of ointments, creams, milks, pomades, powders, impregnated pads, syndets, solutions, gels, sprays, mousses, lotions, suspensions, sticks, shampoos or washing bases. They may also be in the form of suspensions of microspheres or nanospheres or lipid or polymeric vesicles, or of polymeric or gelled patches, or of hydrogels allowing controlled release of the active compounds. These topical compositions may moreover be either in anhydrous form or in an aqueous form.

The composition according to the invention preferentially comprises between 0.001% and 5% of said compound of formula (I) or a pharmaceutically acceptable salt thereof, by weight relative to the total weight of the composition.

The amount effectively administered to be used according to the invention depends on the desired therapeutic effect, and may thus vary within a wide range. A person skilled in the art, in particular a medical practitioner, can readily, on the basis of his general knowledge, determine the appropriate amounts.

The composition according to the invention may comprise at least one other active ingredient.

The additional active ingredient is preferentially chosen from the group comprising, but without being limited thereto, antibiotics, antibacterials, antivirals, antiparasitic agents, antifungal agents, anesthetics, analgesics, antiallergic agents, retinoids, free-radical scavengers, antiprurigi-nous agents, antihistamines, immunosuppressants, corticosteroids, keratolytic agents, intravenous immunoglobulins, antiangiogenic agents, antiinflammatory agents and/or a mixture thereof.

More preferentially, the additional active ingredient is known for its efficacy in treating dermatological complaints associated with a keratinization disorder with a proliferative, inflammatory and/or immunoallergic component, such as psoriasis, atopic dermatitis, actinic keratosis or acne.

As nonlimiting examples of additional active ingredients, mention may be made of ingredients chosen from betamethasone dipropionate glycol, clobetasol 17-propionate, halobetasol propionate, amcinonide, desoximetasone, diflucortolone valerate, fluocinonide, halcinonide, mometasone furoate, triamcinolone acetonide, beta methasone valerate, clobetasone 17-butyrate, desonide, hydrocortisone 17-valerate, prednicarbate, hydrocortisone, hydrocortisone acetate, calcipotriol, calcitriol, adapalene, benzoyl peroxide, clindamycin and erythromycin.

The present invention relates to novel mTOR-inhibiting compounds of formula (I).

Thus, one aspect of the present invention is the compounds of formula (I) as described above which are intended to be used as medicaments.

An aspect of the invention is also a composition according to the invention for its use as a medicament, in particular in the treatment of diseases involving an mTOR enzyme with serine-threonine kinase activity in a patient.

The terms "treating" or "treatment" as used in the present invention relate to the inversion, attenuation, inhibition of progression, delay of onset, improvement and/or partial or total relief of a disease or a disorder or of one or more symptoms of the disease or of the disorder, as described hereinbelow. In certain embodiments, the treatment may be administered after one or more symptoms have developed. In certain particular embodiments, the treatment may be administered as a preventive measure, for preventing or stopping the progression of a disease or a disorder. In this context, the term "prevention" denotes a reduction of the risk of acquiring a given disease or disorder. In other embodiments, the treatment may be administered in the absence of symptoms. For example, the treatment may be administered to a predisposed individual before the appearance of the symptoms (for example in the light of a history of symptoms and/or of genetic factors or other predisposing factors). The treatment may also be continued after the disappearance of the symptoms, for example to prevent or delay their reappearance. Thus, in certain embodiments, the term "treatment" comprises the prevention of relapse or of recurrence of a disease or a disorder.

As used in the present invention, the term "patient" denotes a mammal and includes human and animal individuals, preferably a human.

The composition according to the invention is more particularly intended to be used in the treatment of dermatological complaints associated with a keratinization disorder with a proliferative, inflammatory and/or immunoallergic component.

The dermatological complaints associated with a keratinization disorder with a proliferative, inflammatory and/or immunoallergic component comprise keratinization conditions or disorders relating to cell proliferation, notably common acne, comedones, polymorphs, acne rosacea, nodulocystic acne, acne conglobata, senile acne, and secondary acnes such as solar acne, medication-related acne or occupational acne, other keratinization disorders, notably ichthyosis, ichthyosiform conditions, Darier's disease, palmoplantar keratoderma, leukoplakia and leukoplakiform conditions, and cutaneous or mucous (buccal) lichen, other dermatological complaints associated with a keratinization disorder with an inflammatory and/or immunoallergic component, notably all forms of psoriasis, whether it is cutaneous, mucous or ungual psoriasis, and even psoriatic rheumatism, or cutaneous atopy, such as atopic dermatitis (or atopic eczema) or respiratory atopy or gingival hypertrophy, all dermal or epidermal proliferations, whether benign or malignant, and whether of viral origin or otherwise, such as common warts, flat warts and verruciform epidermodysplasia, oral or florid papillomatoses, and lesions or proliferations that may be induced by ultraviolet radiation, notably in the case of actinic keratoses, and basal cell and spinal cell epithelioma.

More preferentially, the composition according to the invention is intended to be used in the treatment of dermatological complaints associated with a keratinization disorder with a proliferative, inflammatory and/or immunoallergic component, such as psoriasis, atopic dermatitis, actinic keratosis or acne, even more preferentially atopic dermatitis.

More preferentially, the composition according to the invention is intended to be used in the treatment of the inflammatory component of atopic dermatitis, and preferentially the topical treatment of the inflammatory component of atopic dermatitis.

The term "inflammatory component of atopic dermatitis" means an inflammation involving the CD4+ lymphocytes, eosinophils, mastocytes and Th2 cytokines.

Figure 2:
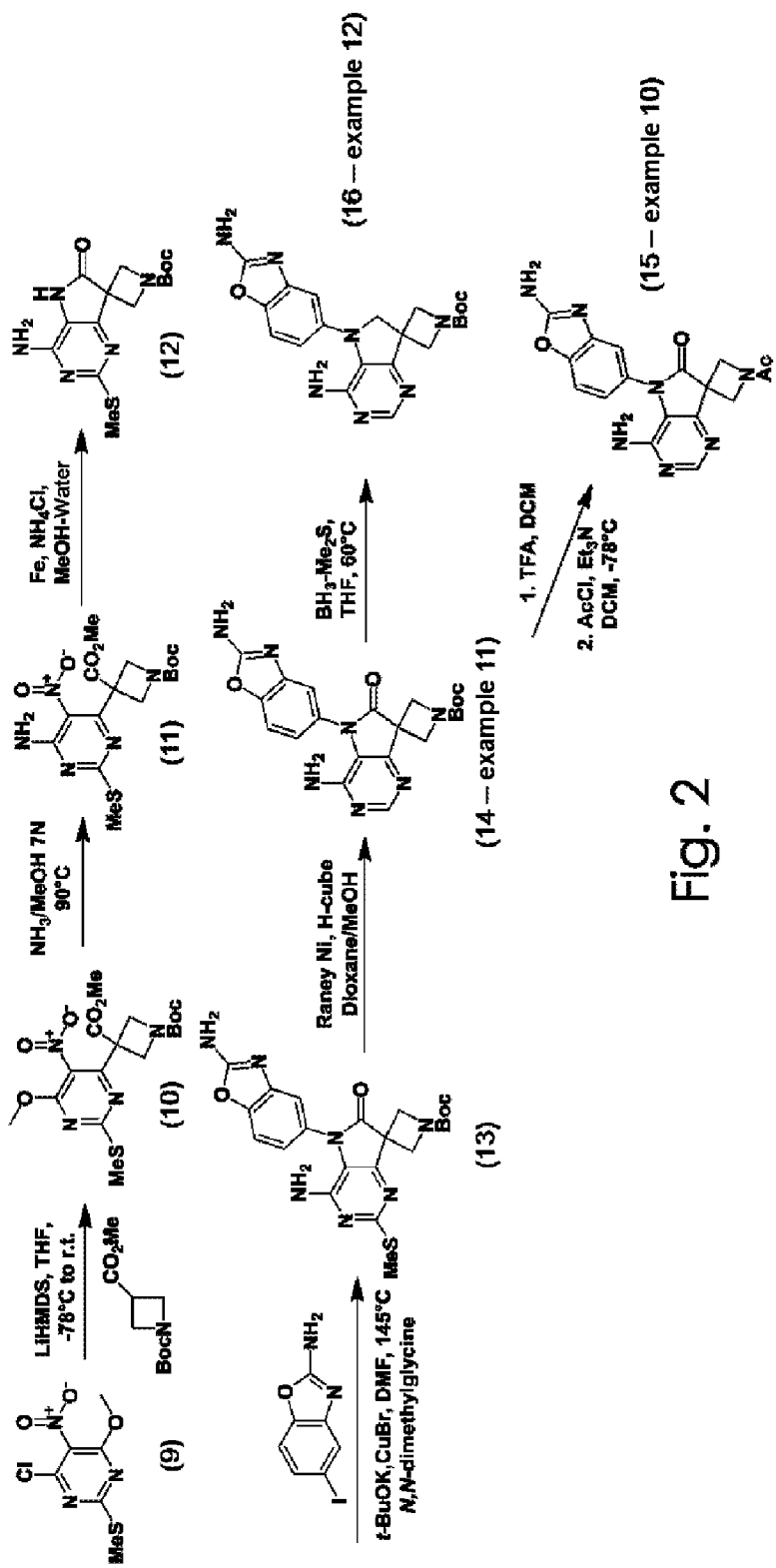
FIG. 2 represents a route for synthesizing the compounds 1-acetyl-4'-amino-5'-(2-aminobenzo[d]oxazol-5-yl)spiro[azetidine-3,7'-pyrrolo[3,2-d]pyrimidin]-6'(5'H)-one (example 10), tert-butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate (example 11) and tert-butyl 4'-amino-5'-(2-aminobenzo[d]oxazol-5-yl)-5',6'-dihydrospiro[azetidine-3,7'-pyrrolo[3,2-d]pyrimidine]-1-carboxylate (example 12).

An aspect of the present invention is also processes for preparing the compounds of formula (I), in particular according to the reaction schemes given in FIGS. 1 and 2.

Several examples of production of active compounds of formula (I) according to the invention and inhibitory activity results will now be given, by way of illustration and with no limiting nature.

Examples 1 and 2: route for synthesizing the compounds 5-(4-amino-7-isobutyl-7-methyl-6,7-dihydro-5H-pyrrolo[3,2-d]pyrimidin-5-yl)benzo[d]oxazol-2-amine (enantiomer 1-e1) and 5-(4-amino-7-isobutyl-7-methyl-6,7-dihydro-5H-pyrrolo[3,2-d]pyrimidin-5-yl)benzo[d]oxazol-2-amine (enantiomer 2-e2) As Illustrated by FIG. 1

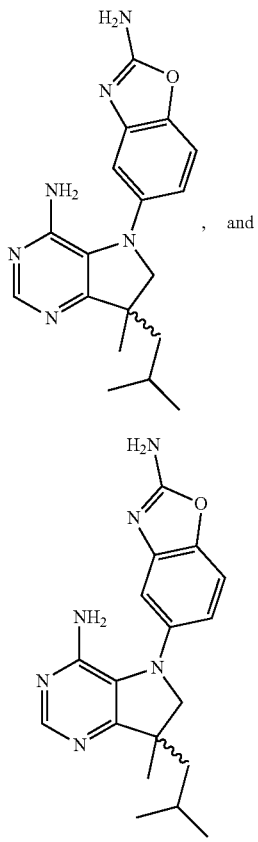

a) Ethyl 2-(6-methoxy-5-nitropyrimidin-4-yl)-2,4-dimethylpentanoate

1-Iodo-2-methylpropane (13.12 ml; 0.11 mol; 1.10 eq.) is added to a suspension of ethyl (6-methoxy-5-nitropyrimidin-4-yl)acetate (25.00 g; 0.10 mol; 1.00 eq.) (1) and cesium carbonate (37.15 g; 0.11 mol; 1.10 eq.) in acetonitrile (250.00 ml). The reaction medium is heated at 70° C. for 12 hours. Cesium carbonate (37.15 g; 0.11 mol; 1.10 eq.) is then added, followed by iodomethane (7.74 ml; 0.12 mol; 1.20 eq.) and the reaction medium is heated at 70° C. for 5 hours. After returning to room temperature, the reaction medium is filtered to remove the cesium carbonate, and the filtrate is then concentrated under vacuum. The residue (33.8 g) is chromatographed on silica gel with solid deposition (puriFlash IR-50SI/800G column, puriFlash) eluted with heptane/ethyl acetate (98/2 to 90/10). Ethyl 2-(6-methoxy-5-nitropyrimidin-4-yl)-2,4-dimethylpentanoate (21.3 g; 66%) (2) is obtained in the form of a clear yellow oil.

b) Ethyl 2-(6-amino-5-nitropyrimidin-4-yl)-2,4-dimethylpentanoate

In an autoclave, 7N ammonia in methanol (216.00 ml) is added to a solution of ethyl 2-(6-methoxy-5-nitropyrimidin-4-yl)-2,4-dimethylpentanoate (21.26 g; 0.07 mol; 1.00 eq.) (2) in methanol (32 ml). The reaction medium is heated at 90° C. for at least 7 hours, for example 24 hours. The solvents are concentrated under vacuum. Ethyl 2-(6-amino-5-nitropyrimidin-4-yl)-2,4-dimethylpentanoate (19 g; 81%) (3) is obtained in the form of a yellow solid without further purification.

c) 7-Isobutyl-7-methyl-6,7-dihydro-5H-pyrrolo[3,2-d]pyrimidin-4-amine

A suspension of sodium dithionite (46.78 g; 0.23 mol; 5.00 eq.) in water (136 ml) is added to a solution, heated to 80° C., of ethyl 2-(6-amino-5-nitropyrimidin-4-yl)-2,4-dimethylpentanoate (15.74 g; 45.68 mmol; 1.00 eq.) (3) in ethanol (271 ml). The reaction medium is heated at 80° C. for at least 1 hour, for example 5 hours. The reaction mixture is returned to room temperature overnight and then filtered through Celite. The filtrate is concentrated under vacuum to give ethyl 2-(6-amino-5-sulfoaminopyrimidin-4-yl)-2,4-dimethylpentanoate (16.00 g; 101%). The product is used directly in the following cyclization step.

4M hydrogen chloride (80.00 ml; 4.00 M; 0.32 mol; 5.00 V) in 1,4-dioxane is added to a suspension of ethyl 2-(6-amino-5-sulfoaminopyrimidin-4-yl)-2,4-dimethylpentanoate (16.00 g; 45.68 mmol; 1.00 eq.) in 1,4-dioxane (320.00 ml). The white suspension is stirred at room temperature for 30 minutes. A portion of the hydrochloric acid is removed under a stream of nitrogen and the reaction medium is diluted and then poured onto an ice/32% aqueous ammonia solution to neutralize it. The product is extracted with ethyl acetate/n-butanol (90/10). The organic phases are combined, washed with saturated sodium chloride solution, dried over magnesium sulfate, filtered and evaporated under vacuum. Several coevaporations with heptane are performed to entrain the n-butanol. 4-Amino-7-isobutyl-7-methyl-5,7-dihydro-6H-pyrrolo[3,2-d]pyrimidin-6-one (11.30 g; 105.07%) (4) is obtained in the form of a pale yellow solid.

A solution of lithium aluminum hydride in tetrahydrofuran (106.76 ml; 1.00 M; 0.11 mol; 2.20 eq.) is added dropwise at 0° C. to a solution of 4-amino-7-isobutyl-7-methyl-5,7-dihydro-6H-pyrrolo[3,2-d]pyrimidin-6-one (11.30 g; 45.68 mmol; 1.00 eq.) (4) in tetrahydrofuran (267 ml). After returning to room temperature, the reaction mixture is heated at 90° C. for 7 hours. The reaction medium is cooled to 0° C. 4.2 ml of water, 4.2 ml of aqueous 15% sodium hydroxide solution (3N) and then 12.6 ml of water are added dropwise, stirring is continued for 30 minutes at room temperature and then 160 ml of ethyl acetate are added. Magnesium sulfate is added to dry the organic phase, and the reaction medium is stirred for a further 40 minutes. The precipitate is filtered off on Celite and the filtrate is evaporated under vacuum to give 7-isobutyl-7-methyl-6,7-dihydro-5H-pyrrolo[3,2-d]pyrimidin-4-ylamine (8.6 g; 91%) (5) in the form of a beige-colored solid.

d) 7-isobutyl-7-methyl-5-(2-methylbenzo[d]oxazol-5-yl)-6,7-dihydro-5H-pyrrolo[3,2-d]pyrimidin-4-amine 7-Isobutyl-7-methyl-6,7-dihydro-5H-pyrrolo[3,2-d]pyrimidin-4-ylamine (1.00 g; 4.50 mmol; 1.00 eq.) (5) and 5-bromo-2-methylbenzoxazole (1.14 g; 5.40 mmol; 1.20 eq.) are placed in a round-bottomed flask in the presence of toluene and evaporated to dryness (2×) to remove all traces of water. Sodium tert-butoxide (1.30 g; 13.50 mmol; 3.00 eq.) and then a mixture of 2-dicyclohexylphosphino-2',6'-diisopropoxybiphenyl (RuPhos) (419.84 mg; 0.90 mmol; 0.20 eq.) and the chloro-(2-dicyclohexylphosphino-2',6'-diisopropoxy-1,1'-biphenyl) [2-(2-aminoethyl) phenyl]palladium(II)-methyl-t-butyl ether adduct (RuPhos Pd G1 Methyl t-Butyl Ether adduct) (734.89 mg; 0.90 mmol; 0.20 eq.) are added to the above mixture dissolved in toluene (37 ml). The reaction mixture is heated at 100° C. for 4 hours. The reaction medium is hydrolyzed and then diluted with ethyl acetate. The product is extracted with ethyl acetate. The organic phases are combined, washed once with water, once with saturated sodium chloride solution, dried over magnesium sulfate, filtered and evaporated under vacuum. The crude product, obtained in the form of a blood-red paste, is chromatographed on silica gel with solid deposition (puriFlash IR-5051/300G column, CombiFlash), eluting with dichloromethane/methanol (99/1 to 95/5). 7-Isobutyl-7-methyl-5-(2-methyl benzoxazol-5-yl)-6,7-dihydro-5H-pyrrolo[3,2-d]pyrimidin-4-ylamine (1.1 g; 70%) (6) is obtained in the form of a dark orange foam.

e) 5-(4-amino-7-isobutyl-7-methyl-6,7-dihydro-5H-pyrrolo[3,2-d]pyrimidin-5-yl) benzo[d]oxazol-2-amine 35% hydrochloric acid solution (41.60 ml) is added to a solution of 7-isobutyl-7-methyl-5-(2-methyl benzoxazol-5-yl)-6,7-dihydro-5H-pyrrolo[3,2-d]pyrimidin-4-ylamine (2.08 g; 6.16 mmol; 1.00 eq.) (6) in an ethanol (41.60 ml)/water (41.60 ml) mixture. The reaction medium is heated at 40° C. for 4 hours. The solvents are then removed under vacuum to recover the product in water. The medium is poured into a mixture of 300 ml of ice/30 ml of aqueous 32% ammonia solution. The product is extracted with an ethyl acetate/n-butanol (90/10) mixture (2×). The organic phases are combined, washed once with saturated sodium chloride solution, dried over magnesium sulfate, filtered and evaporated under vacuum. 2-Amino-4-(4-amino-7-isobutyl-7-methyl-6,7-dihydro-5H-pyrrolo[3,2-d]pyrimidin-5-yl) phenol (7) is obtained in the form of a red foam and is used directly in the next step.
Di(1H-imidazol-1-yl)methanimine (2.09 g; 12.98 mmol; 1.80 eq.) is added to a solution of crude 2-amino-4-(4-amino-7-isobutyl-7-methyl-6,7-dihydro-5H-pyrrolo[3,2-d]pyrimidin-5-yl)phenol (2.26 g; 6.16 mmol; 1.00 eq.) (7) in tetrahydrofuran (34 ml). The reaction medium is heated at 70° C. for 8 hours. After returning to room temperature, the medium is poured into water and ethyl acetate. The two phases are separated and the aqueous phase is extracted with ethyl acetate. The organic phases are combined, washed with water, dried over magnesium sulfate, filtered and evaporated. The residue is chromatographed on silica gel with solid deposition (puriFlash IR-50S1/120G column, CombiFlash) eluted with dichloromethane/methanol (97/3). 5-(4-Amino-7-isobutyl-7-methyl-6,7-dihydro-5H-pyrrolo[3,2-d]pyrimidin-5-yl)benzo[d]oxazol-2-amine (1.9 g; 90%) (8) is obtained in the form of a beige-colored solid for separation by SFC of the two enantiomers. The two enantiomers are obtained in a yield of 36% by chiral separation under the following conditions: Column: ID (Chiral Technologies) 150 mm*3 mm, 3 μm; temperature: 35° C.; $CO_2$ pressure: 104 bar; cosolvent: 25% methanol; total flow rate: 1.5 ml/min.

Enantiomer 1 (example 1) of 5-(4-amino-7-isobutyl-7-methyl-6,7-dihydro-5H-pyrrolo[3,2-d]pyrimidin-5-yl)benzo[d]oxazol-2-amine corresponds to a retention time of 2.8 minutes.

1H NMR (DMSO-d6) δ: 0.70 (d, J=6.4 Hz, 3H), 0.83 (d, J=6.4 Hz, 3H), 1.19 (s, 3H), 1.30-1.46 (m, 1H), 1.57-1.72 (m, 2H), 3.73 (d, J=10.5 Hz, 1H), 3.84 (d, J=10.5 Hz, 1H), 5.74 (s, 2H), 6.44 (dd, J=8.5, 2.2 Hz, 1H), 6.62 (d, J=2.4 Hz, 1H), 7.23 (d, J=8.4 Hz, 1H), 7.35 (s, 2H), 8.12 (s, 1H)

MS (ESI) m/z=339 [M+H]+

Enantiomer 2 (example 2) of 5-(4-amino-7-isobutyl-7-methyl-6,7-dihydro-5H-pyrrolo[3,2-d]pyrimidin-5-yl) benzo[d]oxazol-2-amine corresponds to a retention time of 3.7 minutes.

1H NMR (DMSO-d6) δ: 0.70 (d, J=6.4 Hz, 3H), 0.83 (d, J=6.4 Hz, 3H), 1.19 (s, 3H), 1.30-1.46 (m, 1H), 1.57-1.72 (m, 2H), 3.73 (d, J=10.5 Hz, 1H), 3.84 (d, J=10.5 Hz, 1H), 5.74 (s, 2H), 6.44 (dd, J=8.5, 2.2 Hz, 1H), 6.62 (d, J=2.4 Hz, 1H), 7.23 (d, J=8.4 Hz, 1H), 7.35 (s, 2H), 8.12 (s, 1H)

MS (ESI) m/z=339 [M+H]+

Example 3: 5-(2-aminobenzoxazol-5-yl)-7-isobutyl-6,7-dihydro-5H-pyrrolo[3,2-d]pyrimidin-4-ylamine

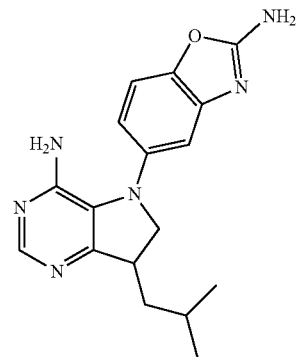 [SMILES: CC(C)CC1CN(c2ccc3oc(N)nc3c2)c2c(N)ncnc21]

This compound may be obtained according to the process presented in FIG. 1.

$^1$H NMR (Methanol-d4) δ: 1.00 (d, J=8.3 Hz, 6H), 1.34 (br s, 1H), 1.90 (dd, J=13.8, 7.1 Hz, 1H), 2.37 (br s, 2H), 3.39 (m, 2H), 7.14 (d, J=9.2 Hz, 1H), 7.29 (br s, 2H), 7.39 (d, J=8.8 Hz, 1H) MS (ESI) m/z=325 [M+H]+

Example 4: 5-(2-aminobenzoxazol-5-yl)-7-methyl-7-methylsulfanylmethyl-6,7-dihydro-5H-pyrrolo[3,2-d]pyrimidin-4-ylamine

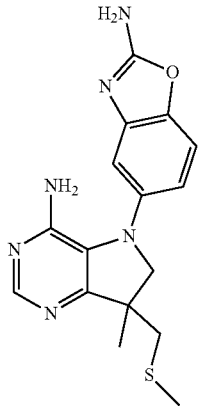

This compound may be obtained according to the process presented in FIG. 1.

$^1$H NMR (Methanol-d4) δ: 1.39 (s, 3H), 1.99 (s, 3H), 2.76-2.93 (m, 2H), 3.78 (d, J=10.4 Hz, 1H), 4.09 (d, J=10.5 Hz, 1H), 6.67 (d, J=8.6 Hz, 1H), 6.82 (s, 1H), 7.23 (d, J=8.3 Hz, 1H), 8.12 (s, 1H) MS (ESI) m/z=343 [M+H]+

Example 5: route for synthesizing the compound 5-(4-amino-7,7-diethyl-6,7-dihydro-5H-pyrrolo[3,2-d]pyrimidin-5-yl) benzo[d]oxazol-2-amine

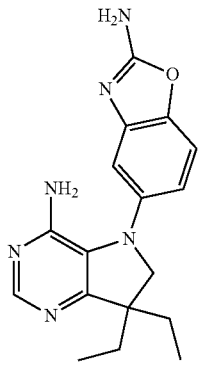 [SMILES: CCC1(CC)CN(c2ccc3oc(N)nc3c2)c2c(N)ncnc21]

a) Ethyl 2-ethyl-2-(6-methoxy-5-nitropyrimidin-4-yl)butanoate

Iodoethane (399.97 μl; 4.98 mmol; 1.20 eq.) is added to a suspension of ethyl (6-methoxy-5-nitropyrimidin-4-yl)acetate (1.00 g; 4.15 mmol; 1.00 eq.) and cesium carbonate (1.42 g; 4.35 mmol; 1.05 eq.) in acetonitrile (15 ml). The reaction medium is heated at 70° C. for 12 hours. Cesium carbonate (1.62 g; 4.98 mmol; 1.20 eq.) is added, followed by iodoethane (499.96 μl; 6.22 mmol; 1.50 eq.) and the reaction medium is heated at 70° C. for 5 hours. After returning to room temperature, the reaction medium is filtered to remove the cesium carbonate, and the filtrate is then concentrated under vacuum. The residue is chromatographed on silica gel (40 g, liquid deposition, heptane/ethyl acetate eluent from 0 to 5% of ethyl acetate, TLC: 50/50 heptane/ethyl acetate Rf=0.8) to give ethyl 2-ethyl-2-(6-methoxy-5-nitropyrimidin-4-yl)butanoate (1.0 g; 81%) in the form of a clear oil.

b) Ethyl 2-(6-amino-5-nitropyrimidin-4-yl)-2,4-dimethylpentanoate

In a sealed microwave tube, 7N ammonia in methanol (3.0 ml) is added to a solution of ethyl 2-ethyl-2-(6-methoxy-5-nitropyrimidin-4-yl)butanoate (1.00 g; 3.36 mmol; 1.00 eq.) in methanol (5.0 ml). The reaction medium is heated at 70° C. for 12 hours. The solvents are concentrated under vacuum. Ethyl 2-(6-amino-5-nitropyrimidin-4-yl)-2-ethylbutanoate (950 mg) is obtained in the form of a yellow solid without further purification.

c) 4-amino-7,7-diethyl-5,7-dihydro-6H-pyrrolo[3,2-d]pyrimidin-6-one

A suspension of ethyl 2-(6-amino-5-nitropyrimidin-4-yl)-2-ethylbutanoate (0.95 g; 3.37 mmol; 1.00 eq.) in ethanol (38.00 ml) is added to a solution, heated to 80° C., of sodium dithionite (2.93 g; 16.83 mmol; 5.00 eq.) in water (9.50 ml). The reaction medium is heated at 80° C. for 1 hour 15 minutes. The reaction mixture is returned to room temperature and then filtered to remove the insoluble matter. The filtrate is concentrated under vacuum to give 4-amino-6-(3-(ethoxycarbonyl)penta n-3-yl)pyrimidin-5-yl)sulfamic acid (1.12 g; 100.13%) in the form of a white solid (presence of salts). The product is used directly in the cyclization step, assuming a quantitative yield.

4M hydrogen chloride in 1,4-dioxane (11.2 ml) is added to a suspension of (4-amino-6-(3-(ethoxycarbonyl)penta n-3-yl)pyrimidin-5-yl)sulfamic acid (1.12 g; 3.37 mmol; 1.00 eq.) in 1,4-dioxane (34 ml). The white suspension is stirred at room temperature for 30 minutes. A portion of the hydrochloric acid is removed under a stream of nitrogen and the reaction medium is diluted and then poured onto an ice/32% aqueous ammonia solution to neutralize it. The product is extracted with ethyl acetate/n-butanol (90/10). The organic phases are combined, washed with saturated sodium chloride solution, dried over magnesium sulfate, filtered and evaporated under vacuum. Several coevaporations with heptane are performed to entrain the n-butanol. 4-Amino-7,7-diethyl-5,7-dihydro-6H-pyrrolo[3,2-d]pyrimidin-6-one (690 mg; 99%) is obtained in the form of a pale yellow solid.

d) 7,7-diethyl-6,7-dihydro-5H-pyrrolo[3,2-d]pyrimidin-4-amine

A solution of lithium aluminum hydride in tetrahydrofuran (7.36 ml; 1.00 M; 7.36 mmol; 2.20 eq.) is added dropwise at 0° C. to a solution of 4-amino-7,7-diethyl-5,7-dihydro-6H-pyrrolo[3,2-d]pyrimidin-6-one (690.00 mg; 3.35 mmol; 1.00 eq.) in tetrahydrofuran (18 ml). After returning to room temperature, the reaction mixture is heated at 90° C. for 7 hours. The reaction medium is cooled to 0° C. 0.3 ml of water, 0.3 ml of aqueous 15% sodium hydroxide solution (3N) and then 0.9 ml of water are added dropwise, stirring is continued for 30 minutes at room temperature and then 5 ml of ethyl acetate are added. Magnesium sulfate is added to dry the organic phase, and the reaction medium is stirred fora further 40 minutes. The precipitate is filtered off on Celite and the filtrate is evaporated under vacuum. The crude reaction product is purified on normal phase (25 g, liquid deposition, dichloromethane/methanol eluent from 3% to 7% of methanol, TLC: 95/5 dichloromethane/methanol Rf=0.2) to give 7,7-diethyl-6,7-dihydro-5H-pyrrolo[3,2-d] pyrimidin-4-amine (480 mg; 75%) in the form of a beige-colored solid.

e) 7,7-diethyl-5-(2-methyl benzo[d]oxazol-5-yl)-6,7-dihydro-5H-pyrrolo[3,2-d]pyrimidin-4-amine 7,7-Diethyl-6,7-dihydro-5H-pyrrolo[3,2-d]pyrimidin-4-amine (200.00 mg; 1.04 mmol; 1.00 eq.) and 5-bromo-2-methylbenzoxazole (242.64 mg; 1.14 mmol; 1.10 eq.) are placed in a round-bottomed flask in the presence of toluene and evaporated to dryness (2×) to remove all traces of water. Sodium tert-butoxide (242.64 mg; 1.14 mmol; 1.10 eq.) and then a mixture of 2-dicyclohexylphosphino-2',6'-diisopropoxybiphenyl (RuPhos) (127.45 mg; 0.16 mmol; 0.15 eq.) and of the chloro-(2-dicyclohexylphosphino-2',6'-diisopropoxy-1,1'-biphenyl) [2-(2-aminoethyl) phenyl]palladium (II)-methyl t-butyl ether adduct (RuPhos Pd G1 Methyl t-Butyl Ether adduct) (127.45 mg; 0.16 mmol; 0.15 eq.) are added to the above mixture dissolved in toluene (8 ml). The reaction mixture is heated at 100° C. for 4 hours. The reaction medium is hydrolyzed and then diluted with ethyl acetate. The product is extracted with ethyl acetate. The organic phases are combined, washed once with water, once with saturated sodium chloride solution, dried over magnesium sulfate, filtered and evaporated under vacuum. The crude product, obtained in the form of a paste, is chromatographed on silica gel with solid deposition, eluting with dichloromethane/methanol (99/1 to 95/5). 7,7-Diethyl-5-(2-methyl benzo[d]oxazol-5-yl)-6,7-dihydro-5H-pyrrolo[3,2-d]pyrimidin-4-amine (28 mg; 8.32%) is obtained in the form of a pink solid.

f) 2-amino-4-(4-amino-7,7-diethyl-6,7-dihydro-5H-pyrrolo[3,2-d]pyrimidin-5-yl) phenol 35% hydrochloric acid solution (0.56 ml) is added to 7,7-diethyl-5-(2-methylbenzoxazol-5-yl)-6,7-dihydro-5H-pyrrolo[3,2-d]pyrimidin-4-ylamine (28.00 mg; 0.09 mmol; 1.00 eq.) dissolved in ethanol (1.12 ml) and water (1.12 ml). The reaction medium is heated at 70° C. for 5 hours. The solvents are removed under vacuum to recover the product in water. The reaction medium is poured into aqueous 15% $NH_3$ solution at 0° C. and the pH is then adjusted to pH=8 with aqueous 32% $NH_3$ solution. The product is extracted with a dichloromethane/n-butanol (80/20) mixture (2×). The organic phases are combined, washed once with water and then dried over magnesium sulfate, filtered and concentrated under vacuum. 2-Amino-4-(4-amino-7,7-diethyl-6,7-dihydro-5H-pyrrolo[3,2-d]pyrimidin-5-yl)phenol (26.00 mg; 100%) is obtained in the form of a pink solid and is used directly in the next step.

g) 5-(4-Amino-7,7-diethyl-6,7-dihydro-5H-pyrrolo[3,2-d]pyrimidin-5-yl) benzo[d]oxazol-2-amine Di(1H-imidazol-1-yl)methanimine (35.0 mg; 0.22 mmol; 2.50 eq.) is added to a solution of crude 2-amino-4-(4-amino-7,7-diethyl-6,7-dihydro-5H-pyrrolo[3,2-d]pyrimidin-5-yl)phenol (26.0 mg; 0.09 mmol; 1.00 eq.) in tetrahydrofuran (1.6 ml). The reaction medium is heated at 70° C. for 8 hours. After returning to room temperature, the medium is poured into water and ethyl acetate. The two phases are separated and the aqueous phase is extracted with ethyl acetate. The organic phases are combined, washed with water, dried over magnesium sulfate, filtered and evaporated. The residue is chromatographed on silica gel with solid deposition and eluted with dichloromethane/methanol (99/1 to 94/6). 5-(4-Amino-7,7-diethyl-6,7-dihydro-5H-pyrrolo[3,2-d]pyrimidin-5-yl)benzo[d]oxazol-2-amine (10 mg; 32%) is obtained in the form of a white solid.

1H NMR (DMSO-d6) δ: 0.69 (t, J=7.4 Hz, 7H), 1.49-1.67 (m, 5H), 3.75 (s, 1H), 5.70 (s, 2H), 6.42 (dd, J=8.5, 2.3 Hz, 1H), 6.60 (d, J=2.4 Hz, 1H), 7.23 (d, J=8.5 Hz, 1H), 7.34 (s, 2H), 8.12 (s, 1H)

MS (ESI) m/z=325 [M+H]+

Example 6: 5-(2-aminobenzoxazol-5-yl)-7,7-dimethyl-6,7-dihydro-5H-pyrrolo[3,2-d]pyrimidin-4-ylamine

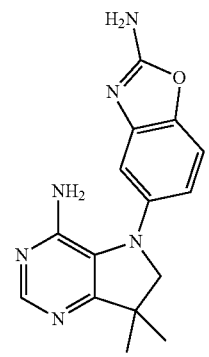 [SMILES: CC1(C)CN(c2ccc3oc(N)nc3c2)c2c(N)ncnc21]

This compound may be obtained according to the process presented in FIG. 1.

$^1$H NMR (DMSO-d6) δ: 1.18 (s, 6H), 3.71 (s, 2H), 5.79 (s, 2H), 6.43 (dd, J=8.4, 2.3 Hz, 1H), 6.61 (d, J=2.3 Hz, 1H), 7.22 (d, J=8.4 Hz, 1H), 7.36 (s, 2H), 8.13 (s, 1H)

MS (ESI) m/z=297 [M+H]+

Example 7: 5-(2-aminobenzoxazol-5-yl)-7-methyl-7-propyl-6,7-dihydro-5H-pyrrolo[3,2-d]pyrimidin-4-ylamine

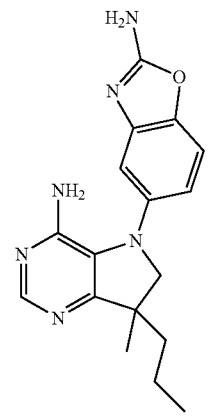

This compound may be obtained according to the process presented in FIG. 1.

$^1$H NMR (DMSO-d6) δ: 0.78 (t, J=7.2 Hz, 3H), 1.20 (s, 3H), 1.22-1.32 (m, 2H) 1.35-1.45 (m, 1H) 1.43-1.57 (m, 1H), 3.69 (d, J=10.7 Hz, 1H), 3.79 (d, J=10.7 Hz, 1H), 5.73

(s, 2H), 6.42 (dd, J=8.6, 2.1 Hz, 1H), 6.61 (d, J=2.3 Hz, 1H), 7.23 (d, J=8.3 Hz, 1H), 7.35 (s, 2H), 8.12 (s, 1H) MS (ESI) m/z=325 [M+H]+

Example 8: 5-(2-aminobenzoxazol-5-yl)-7,7-diethyl-6-methyl-6,7-dihydro-5H-pyrrolo[3,2-d]pyrimidin-4-ylamine

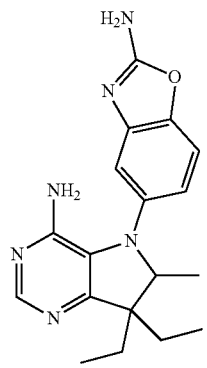 [SMILES: CCC1(CC)c2ncnc(N)c2N(c2ccc3oc(N)nc3c2)C1C]

This compound may be obtained according to the process presented in FIG. 1.

¹H NMR (DMSO-d6) δ: 0.77 (t, J=7.4 Hz, 3H), 0.84 (t, J=7.4 Hz, 3H), 1.21 (d, J=6.6 Hz, 3H), 1.49 (m, 2H), 1.73 (m, 2H), 3.61 (m, 1H), 5.36 (s, 2H), 6.53-6.64 (m, 1H), 6.76 (d, J=2.2 Hz, 1H), 7.27 (d, J=8.4 Hz, 1H), 7.42 (s, 2H), 8.09 (s, 1H)

MS (ESI) m/z=339 [M+H]+

Example 9: 4-amino-5-(2-aminobenzoxazol-5-yl)-7,7-dimethyl-5,7-dihydropyrrolo[3,2-d]pyrimidin-6-one

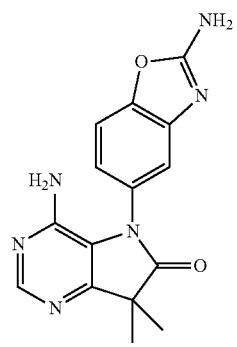 [SMILES: CC1(C)C(=O)N(c2ccc3oc(N)nc3c2)c2c(N)ncnc21]

This compound may be obtained according to the process presented in FIG. 1.

¹H NMR (DMSO-d6) δ: 1.35 (s, 6H), 5.44 (s, 2H), 7.01 (dd, J=8.3, 2.2 Hz, 1H), 7.27 (d, J=2.1 Hz, 1H), 7.45 (d, J=8.3 Hz, 1H), 7.62 (s, 2H), 8.25 (s, 1H) MS (ESI) m/z=311 [M+H]+

Examples 10, 11 and 12: route for synthesizing the compounds 1-acetyl-4'-amino-5'-(2-aminobenzo[d]oxazol-5-yl)spiro[azetidine-3,7'-pyrrolo[3,2-d]pyrimidin]-6'(5'H)-one (15-example 10), tert-butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate (14-example 11) and tert-butyl 4'-amino-5'-(2-aminobenzo[d]oxazol-5-yl)-5',6'-dihydrospiro[azetidine-3,7'-pyrrolo[3,2-d]pyrimidine]-1-carboxylate (16-example 12) as Illustrated in FIG. 2

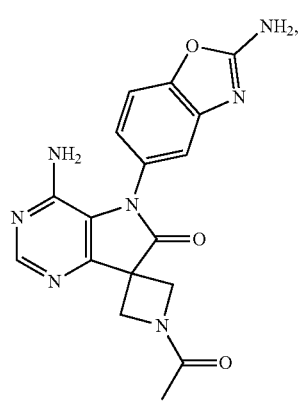

((15)-example10)

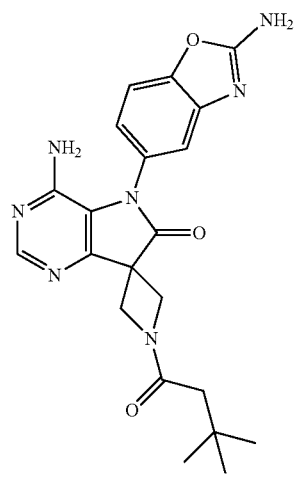

((14)-example11)

and

-continued ((16)-example12)

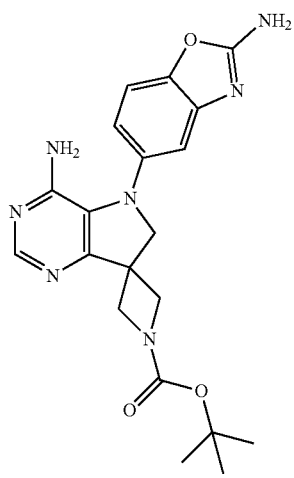

a) 5-Iodo-1,3-benzoxazol-2-amine

In a sealed tube, 5-bromo-1,3-benzoxazol-2-amine (1.0 g, 4.69 mmol), sodium iodide (1.77 g, 11.73 mmol), copper (I) iodide (225 mg, 1.17 mmol) and N,N'-dimethylethylenediamine (414 mg, 4.69 mmol) are stirred in 30 ml of dioxane at 120° C. overnight. Copper (I) iodide (224 mg) and N,N'-dimethylethylenediamine (0.25 ml) are added and stirring is continued for 24 hours at 120° C. After cooling, 100 ml of EtOAc are added and the medium is filtered. The filtrate is made up to 100 ml with water and transferred into a separating funnel. The phases are separated and the aqueous phase is extracted twice with EtOAc. The combined organic fractions are washed with water, with brine, dried over $Na_2SO_4$ and evaporated to dryness. The solid residue is purified by chromatography on silica gel, eluting with DCM, to obtain 5-iodo-1,3-benzoxazol-2-amine (318 mg, 25%).

b) 4-chloro-6-methoxy-2-methylsulfanyl-5-nitropyrimidine (9)

4,6-Dichloro-2-methylsulfanyl-5-nitropyrimidine (10.0 g, 41.6 mmol) in 102 ml of methanol are added slowly (9.49 ml, 41.6 mmol) of sodium methoxide at 30% by weight (a pale yellow precipitate forms). The reaction medium is cooled to 0° C. and the precipitate is filtered off and then rinsed twice with methanol and dried in a vacuum oven at 40° C. to give 4.62 g of a pale yellow powder. The filtrate is concentrated to dryness and then resuspended in water, filtered and dried in a vacuum oven at 40° C. to obtain a further 5.5 g of pale yellow powder. The two fractions obtained contain 70% of the expected product (4-chloro-6-methoxy-2-methylsulfanyl-5-nitropyrimidine—(9)) and 30% of the dimethoxy analog.

c) 1-(cert-butyl) 3-methyl 3-(6-methoxy-2-(methylthio)-5-nitropyrimidin-4-yl)azetidine-1,3-dicarboxylate (10)

To a solution of 4-chloro-6-methoxy-2-methylsulfanyl-5-nitropyrimidine (4.27 g, 17.2 mmol, 1.0 eq.) (9) in tetrahydrofuran (86 ml) is added 1-(tert-butyl) 3-methyl azetidine-1,3-dicarboxylate (3.56 ml, 18.08 mmol, 1.1 eq.). The resulting heterogeneous mixture was cooled to −78° C. and 1M LiHMDS in THF (18.07 ml, 18.08 mmol, 1.1 eq.) was then added dropwise and the reaction mixture was stirred at room temperature for 22 hours. The reaction mixture was poured slowly into water and ethyl acetate. The layers were separated and the aqueous layer was subjected to re-extraction with ethyl acetate. The combined organic layers were washed with water and brine, dried over $Na_2SO_4$ and concentrated under reduced pressure. The crude product was purified by flash chromatography on silica gel using dichloromethane in heptane from 50% to 100% to give the desired compound (1-(tert-butyl) 3-methyl 3-(6-methoxy-2-(methylthio)-5-nitropyrimidin-4-yl)azetidine-1,3-dicarboxylate (10)) in the form of a yellow powder (4.73 g, 66% yield).

d) 1-(cert-butyl) 3-methyl 3-(6-amino-2-(methylthio)-5-nitropyrimidin-4-yl)azetidine-1,3-dicarboxylate (11)

1-(cert-Butyl) 3-methyl 3-(6-methoxy-2-(methylthio)-5-nitropyrimidin-4-yl)azetidine-1,3-dicarboxylate (4.71 g, 11.36 mmol, 1.0 eq.) (10) was diluted in a 7N solution of ammonia in methanol (38 ml, 266 mmol, 20.0 eq.). The resulting suspension was stirred for 3 hours 30 minutes at room temperature. The precipitate formed was then filtered off and washed with methanol to give the expected compound (1-(cert-butyl) 3-methyl 3-(6-amino-2-(methylthio)-5-nitropyrimidin-4-yl)azetidine-1,3-dicarboxylate (11)) in the form of a white powder (3.75 g, 78% yield).

e) tert-Butyl 4'-amino-2'-(methylthio)-6'-oxo-5',6'-dihydrospiro[azetidine-3,7'-pyrrolo[3,2-d]pyrimidine]-1-carboxylate (12)

To a suspension of 1-(cert-butyl) 3-methyl 3-(6-amino-2-(methylthio)-5-nitropyrimidin-4-yl)azetidine-1,3-dicarboxylate (3.53 g, 8.84 mmol, 1.0 eq.) (11) in methanol (44 ml) was added iron powder (2.47 g, 44.2 mmol, 5.0 eq.), followed by addition of ammonium chloride (2.36 g, 44.2 mmol, 5.0 eq.). The resulting heterogeneous mixture was refluxed for 3 hours 30 minutes. The solution was cooled to room temperature and stirred at this temperature overnight. The mixture was then filtered through talc powder and rinsed several times with methanol. The filtrate was concentrated to dryness and precipitated from water to give the expected compound (tert-butyl 4'-amino-2'-(methylthio)-6'-oxo-5',6'-dihydrospiro[azetidine-3,7'-pyrrolo[3,2-d]pyrimidine]-1-carboxylate (12)) in the form of a beige-colored powder (2.35 g, 79% yield).

f) tert-Butyl 4'-amino-5'-(2-aminobenzo[d]oxazol-5-yl)-2'-(methylthio)-6'-oxo-5',6'-dihydrospiro[azetidine-3,7'-pyrrolo[3,2-d]pyrimidine]-1-carboxylate (13)

To a solution of tert-butyl 4-amino-2-methylsulfanyl-6-oxospiro[5H-pyrrolo[3,2-d]pyrimidine-7,3'-azetidine]-1'-carboxylate (500.0 mg, 1.48 mmol, 1.0 eq.) in 10 ml of dry DMF (10 ml) was added potassium tert-butoxide (532 mg, 4.74 mmol, 3.0 eq.). After stirring for 5 minutes, 5-iodo-1,3-benzoxazol-2-amine (1.16 g, 4.45 mmol, 3.0 eq.) and then N,N-dimethylglycine (519.9 mg, 4.89 mmol, 3.0 eq.) and copper (I) bromide (235 mg, 1.63 mmol, 1.0 eq.) were added to the reaction mixture. The reaction mixture was degassed with argon and the tube was then sealed and heated at 145° C. for 7 hours. Next, 1M $KHSO_4$ solution was added to pH=5 and the mixture was extracted with ethyl acetate. The layers were separated and the aqueous layer was then subjected to re-extraction with ethyl acetate. The combined organic layers were washed with water and brine, dried over $Na_2SO_4$ and concentrated under reduced pressure. The crude product was purified by flash chromatography on silica gel using methanol in dichloromethane from 0% to 10% to obtain tert-butyl 4'-amino-5'-(2-aminobenzo[d]oxazol-5-yl)-2'-(methylthio)-6'-oxo-5',6'-dihydrospiro[azetidine-3,7'-pyrrolo[3,2-d]pyrimidine]-1-carboxylate (148 mg, 21% yield) (13).

g) tert-Butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate (14-Example 11)

A solution of tert-butyl 4'-amino-5'-(2-aminobenzo[d]oxazol-5-yl)-2'-(methylthio)-6'-oxo-5',6'-dihydrospiro[azetidine-3,7'-pyrrolo[3,2-d]pyrimidine]-1-carboxylate (75.0 mg, 0.16 mmol, 1.00 eq.) (13) in 1,4-dioxane/MeOH (1:1, 10 ml) was hydrogenated on an H-CUBE PRO machine using a Raney nickel cartridge (0.5 ml/min, 7 bar, 50° C.). The reaction mixture was evaporated to give the expected compound (tert-butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate (14-example 11)) (50 mg, 74% yield). 1H NMR (DMSO-d6) δ: 1.43 (s, 9H), 4.08 (b, 4H), 5.53 (b, 2H), 7.01 (dd, J=2.05, 8.30 Hz, 1H), 7.26 (d, J=2.05 Hz, 1H), 7.45 (d, J=8.30 Hz, 1H), 7.60 (s, 2H), 8.33 (s, 1H). MS (ESI) m/z=424 [M+H]+ h) 1-acetyl-4'-amino-5'-(2-aminobenzo[d]oxazol-5-yl)spiro[azetidine-3,7'-pyrrolo[3,2-d]pyrimidin]-6'(5'H)-one (15-Example 10)

To a solution of tert-butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate (48.0 mg, 0.11 mmol, 1.0 eq.) (14-example 11) in DCM (1 ml) at 4° C. under $N_2$ was added trifluoroacetic acid (0.5 ml) dropwise. After 4 hours, the reaction mixture was concentrated under vacuum. The residue was dissolved in DCM/MeOH (9/1) and passed through a basic alumina plate using a DCM/MeOH mixture (9/1) as eluent. Fractions containing the expected compound were evaporated and the crude product was used directly in the next step.
To a solution of 4'-amino-5'-(2-amino-1,3-benzoxazol-5-yl)spiro[azetidine-3,7'-pyrrolo[3,2-d]pyrimidine]-6'-one (38.0 mg, 0.12 mmol, 1.0 eq.) in DCM (2 ml) cooled to −78° C. under $N_2$ were respectively added triethylamine (18.2 µl, 0.13 mmol, 1.1 eq.) and acetyl chloride (8.43 µL, 0.12 mmol, 1.0 eq.). The reaction mixture was maintained at −78° C. for 2 hours, and then returned slowly to room temperature. A solution of cold water (4° C.) was then added and the two-phase mixture was stirred for 5 minutes. It was then transferred into a separating funnel, the organic layer was collected and the aqueous phase was extracted twice with DCM. The combined organic layers were dried over sodium sulfate, filtered and dried under vacuum. The solid residue was purified by chromatography on a column of basic alumina using a DCM/MeOH gradient of 98/2 to 9/1. The pure fractions were combined to give the expected compound (1-acetyl-4'-amino-5-(2-aminobenzo[d]oxazol-5-yl) spiro[azetidine-3,7'-pyrrolo[3,2-d]pyrimidin]-6' (5'H)-one (15-example 10)) in the form of a white powder (2.2 mg, 5% yield).

1H NMR (DMSO-d6) δ: 1.86 (s, 3H), 4.09 (b, 2H), 4.38 (b, 2H), 5.51 (b, 2H), 7.03 (dd, J=2.12, 8.20 Hz, 1H), 7.27 (d, J=2.12 Hz, 1H), 7.45 (d, J=8.20 Hz, 1H), 7.61 (s, 2H), 8.33 (s, 1H).
MS (ESI) m/z=366 [M+H]+ h') tert-Butyl 4'-amino-5'-(2-aminobenzo[d]oxazol-5-yl)-2'-(methylthio)-5',6'-dihydrospiro[azetidine-3,7'-pyrrolo[3,2-d]pyrimidine]-1-carboxylate To a solution of tert-butyl 4'-amino-5'-(2-amino-1,3-benzoxazol-5-yl)-2'-methylsulfanyl-6'-oxospiro[azetidine-3,7'-pyrrolo[3,2-d]pyrimidine]-1-carboxylate (145.0 mg, 0.31 mmol, 1.0 eq.) in 3 ml of tetrahydrofuran was added a 2M solution of borane-methyl sulfide complex in dichloromethane (1.39 ml, 2.78 mmol, 1.0 eq.). The reaction mixture was stirred at room temperature overnight and at 60° C. for 1 hour. Water and ethyl acetate were then added. The layers were separated and the aqueous layer was then subjected to re-extraction with ethyl acetate. The combined organic layers were washed with water and brine, dried over $Na_2SO_4$ and concentrated under reduced pressure. The crude product was purified by flash chromatography on silica gel using methanol in dichloromethane from 2% to 15% to obtain the desired compound tert-butyl 4'-amino-5'-(2-aminobenzo[d]oxazol-5-yl)-2'-(methylthio)-5',6'-dihydrospiro[azetidine-3,7'-pyrrolo[3,2-d]pyrimidine]-1-carboxylate (26 mg, 19% yield).

i') tert-Butyl 4'-amino-5'-(2-aminobenzo[d]oxazol-5-yl)-5',6'-dihydrospiro[azetidine-3,7'-pyrrolo[3,2-d]pyrimidine]-1-carboxylate (16-example 12)

tert-Butyl 4'-amino-5'-(2-aminobenzo[d]oxazol-5-yl)-2'-(methylthio)-6'-oxo-5',6'-dihydrospiro[azetidine-3,7'-pyrrolo[3,2-d]pyrimidine]-1-carboxylate (10.0 mg, 0.022 mmol, 1.0 eq.) was dissolved in 4 ml of a 1/1 mixture of 1,4-dioxane and methanol. The resulting solution was filtered through a Millipore filter and hydrogenated in the presence of Raney nickel on an H-CUBE PRO machine (0.5 ml/min, 7 bar, 50° C.). The system was rinsed with 20 ml of DMSO to give a solution containing the expected compound. The volume was reduced under reduced pressure and the oil thus obtained was then purified by chromatography on reverse-phase RP18 using a gradient of the methanol in water of from 30% to 50% to give the desired compound (tert-butyl 4'-amino-5'-(2-aminobenzo[d]oxazol-5-yl)-5',6'-dihydrospiro[azetidine-3,7'-pyrrolo[3,2-d]pyrimidine]-1-carboxylate (16-example 12)) (0.8 mg, 10% yield). 1H NMR (DMSO-d6) δ: 1.46 (s, 9H), 4.04 (b, 2H), 4.20 (s, 2H), 4.26 (b, 2H), 6.71 (dd, J=2.07, 8.41 Hz, 1H), 6.86 (d, J=2.07 Hz, 1H), 7.25 (d, J=8.41 Hz, 1H), 8.19 (s, 1H).

MS (ESI) m/z=410 [M+H]+

Example 13: Enzymatic mTOR and Cellular mTORC1/mTORC2 Activities 13.1 Inhibitory Activity on mTOR Kinase The model for screening the inhibitory activity of the molecules on mTOR was developed with the LANTHASCREEN™ technology (Lifetechnologies). The reaction substrate (400 nM final), the serial dilutions of the molecules (1% DMSO final) and the enzyme (<1 nM) are successively added to a 384-well plate (Corning 4514) in a final volume of 10 μL per well. After 1 hour of reaction at room temperature, 10 μL of a solution containing 10 mM final of EDTA and 2 nM final of terbium-labeled antibodies are added. After at least 30 minutes of incubation at room temperature, the TR-FRET signal is measured with a suitable microplate reader according to the supplier's recommendations. The data are normalized with positive controls ("POS" containing a saturating concentration of reference inhibitor) and negative controls ("NEG" containing 1% DMSO): % inhibition=((X−NEG)*100)/(POS−NEG). The IC50 values are calculated using a 4-parameter logistic model with the aid of the XLFit software (IDBS).

13.2 mTORC$_1$/mTORC$_2$ Inhibitory Activity

A431 cells are seeded in whole medium (DMEM+10% FCS) at 25 000 cells per well in a 96-well plate coated with poly-L-lysine. 24 hours before the experiment, the medium is replaced with serum-free medium. The serial dilutions of the test molecules are added (0.1% DMSO final). After incubation for 3 hours at 37° C., the phosphorylation of the biomarkers S6RP (mTORC$_1$) and AKT (mTORC$_2$) is measured using the HTRF technology (Cisbio) according to the supplier's recommendations. The data are normalized with positive controls ("POS" containing a saturating concentration of reference inhibitor) and negative controls ("NEG" containing 1% DMSO): % inhibition=((X−NEG)*100)/(POS−NEG). The IC50 values are calculated using a 4-parameter logistic model with the aid of the XLFit software (IDBS).

Table of the activity results:

| Example | Chemical name | Ki mTOR (nM) | IC50 mTORC1 (nM) | IC50 mTORC2 (nM) |
|---|---|---|---|---|
| 1 | 5-(2-aminobenzoxazol-5-yl)-7-isobutyl-7-methyl-6,7-dihydro-5H-pyrrolo[3,2-d]pyrimidin-4-ylamine | 2.0 | 1.0 | 2.2 |
| 2 | 5-(2-aminobenzoxazol-5-yl)-7-isobutyl-7-methyl-6,7-dihydro-5H-pyrrolo[3,2-d]pyrimidin-4-ylamine | 130.0 | 68.5 | 136.8 |
| 3 | 5-(2-aminobenzoxazol-5-yl)-7-isobutyl-6,7-dihydro-5H-pyrrolo[3,2-d]pyrimidin-4-ylamine | 11.7 | 1.8 | 11.4 |
| 4 (racemic) | 5-(2-aminobenzoxazol-5-yl)-7-methyl-7-methylsulfanylmethyl-6,7-dihydro-5H-pyrrolo[3,2-d]pyrimidin-4-ylamine | 3.6 | 11.7 | 14.5 |
| 5 | 5-(2-aminobenzoxazol-5-yl)-7,7-diethyl-6,7-dihydro-5H-pyrrolo[3,2-d]pyrimidin-4-ylamine | 34.6 | 8.6 | 16.3 |
| 6 | 5-(2-aminobenzoxazol-5-yl)-7,7-dimethyl-6,7-dihydro-5H-pyrrolo[3,2-d]pyrimidin-4-ylamine | 37.8 | 17.7 | 31.4 |
| 7 | 5-(2-aminobenzoxazol-5-yl)-7-methyl-7-propyl-6,7-dihydro-5H-pyrrolo[3,2-d]pyrimidin-4-ylamine | 8.7 | 19.5 | 34.5 |
| 8 | 5-(2-aminobenzoxazol-5-yl)-7,7-diethyl-6-methyl-6,7-dihydro-5H-pyrrolo[3,2-d]pyrimidin-4-ylamine | 212.7 | 151.6 | 242.8 |
| 9 | 4-amino-5-(2-aminobenzoxazol-5-yl)-7,7-dimethyl-5,7-dihydropyrrolo[3,2-d]pyrimidine-6-one | 55.8 | 38.4 | 176.4 |
| 10 | 1-acetyl-4'-amino-5'-(2-aminobenzo[d]oxazol-5-yl)spiro[azetidine-3,7'-cyclopenta[d]pyrimidin]-6'(5'H)-one | 228.9 | >9999 | >9999 |
| 11 | tert-butyl 4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate | 109.7 | | |
| 12 | tert-butyl 4'-amino-5'-(2-aminobenzo[d]oxazol-5-yl)-5',6'-dihydrospiro[azetidine-3,7'-pyrrolo[3,2-d]pyrimidine]-1-carboxylate | 50.5 | 88.1 | 127.9 |
| enantiomer Example 4 | 5-(2-aminobenzoxazol-5-yl)-7-methyl-7-methylsulfanylmethyl-6,7-dihydro-5H-pyrrolo[3,2-d]pyrimidin-4-ylamine | 51.6 | 82.1 | 158.6 |
| racemic (Examples 1 and 2) | 5-(2-aminobenzoxazol-5-yl)-7-isobutyl-7-methyl-6,7-dihydro-5H-pyrrolo[3,2-d]pyrimidin-4-ylamine | 2.4 | 4.2 | 6.3 |
| other enantiomer Example 4 | 5-(2-aminobenzoxazol-5-yl)-7-methyl-7-methylsulfanylmethyl-6,7-dihydro-5H-pyrrolo[3,2-d]pyrimidin-4-ylamine | 8.0 | 4.7 | 8.3 |

IC50: inhibitor concentration causing 50% inhibition. This is a practical indicator of efficacy.

Ki: dissociation constant of the enzyme-inhibitor complex. This indicates the affinity between the enzyme and the inhibitor (in an inverse manner).

The affinity of an inhibitor for an enzyme is given by the inhibition constant Ki, which represents the inhibitor concentration for which half of the enzymatic sites are occupied. Thus, the affinity of an inhibitor is proportionately greater the smaller the Ki. This inhibition constant, expressed in moles per liter, also corresponds to the dissociation constant of the enzyme-inhibitor complex.

Considering the above results, the compound according to example 1 is seen to have better inhibitory activity on mTOR kinase, on both mTORC$_1$ and mTORC$_2$.

The invention claimed is:

1. An mTOR-inhibiting compound of general formula (I)

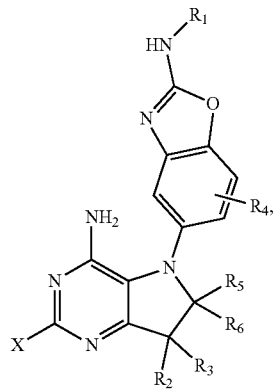

or a pharmaceutically acceptable salt thereof, wherein:
R₁ represents a hydrogen atom;
R₂ and R₃ represent, independently of each other, a hydrogen atom, a halogen atom chosen from Cl and F, a linear or branched $C_1$-$C_6$ alkyl group, optionally interrupted with a heteroatom O, S or —NR₇, or R₂ and R₃ together form a $C_3$-$C_6$ ring or heterocycloalkyl,
wherein R₇ represents a hydrogen atom, a $C_1$-$C_3$ alkyl, acyl, carboxy-tert-butyl or $C_1$-$C_4$ carboxyalkyl group and R₂ and R₃ do not both represent a halogen atom;
R₄ represents a hydrogen atom;
R₅ and R₆ represent, independently of each other, a hydrogen atom, a $C_1$-$C_3$ alkyl group, or R₅ and R₆ together form a carbonyl; and
X represents a hydrogen atom.

2. The mTOR-inhibiting compound according to claim 1, or a pharmaceutically acceptable salt thereof, wherein:
R₂ and R₃ represent, independently of each other, a hydrogen atom, or a linear or branched $C_1$-$C_4$ alkyl group, which is optionally interrupted with a heteroatom S or —NR₇, or R₂ and R₃ together form a $C_4$ heterocycloalkyl,
wherein R₇ represents an acyl or carboxy-tert-butyl group; and
R₅ and R₆ represent, independently of each other, a hydrogen atom, a methyl group, or R₅ and R₆ together form a carbonyl.

3. The mTOR-inhibiting compound according to claim 1, or a pharmaceutically acceptable salt thereof, wherein:
R₁ represents a hydrogen atom;
R₂ represents a methyl group;
R₃ represents a linear or branched $C_1$-$C_4$ alkyl group, optionally interrupted with an S heteroatom;
R₄ represents a hydrogen atom;
R₅ and R₆ represent a hydrogen atom; and
X represents a hydrogen atom.

4. A composition comprising, in a physiologically acceptable medium, an mTOR-inhibiting compound according to claim 1, or a pharmaceutically acceptable salt thereof.

5. The composition according to claim 4, comprising between 0.001% and 5% of the compound by weight relative to the total weight of the composition.

6. The composition according to claim 4, in a form suitable for oral or topical administration.

7. The composition as claimed in claim 6, in a form suitable for topical administration.

8. The compound according to claim 1 selected from the following compounds:
5-(4-Amino-7-isobutyl-7-methyl-6,7-dihydro-5H-pyrrolo[3,2-d]pyrimidin-5-yl)benzo[d]oxazol-2-amine of formula e1 or formula e2;

wherein R is a methyl and R' is an isobutyl group;
5-(2-Amino-benzooxazol-5-yl)-7-isobutyl-6,7-dihydro-5H-pyrrolo[3,2-d]pyrimidin-4-ylamine;
5-(2-Amino-benzooxazol-5-yl)-7-methyl-7-methylsulfanylmethyl-6,7-dihydro-5H-pyrrolo[3,2-d]pyrimidin-4-ylamine;
5-(4-Amino-7,7-diethyl-6,7-dihydro-5H-pyrrolo[3,2-d]pyrimidin-5-yl)benzo[d]oxazol-2-amine;
5-(2-Amino-benzooxazol-5-yl)-7,7-dimethyl-6,7-dihydro-5H-pyrrolo[3,2-d]pyrimidin-4-ylamine;
5-(2-Amino-benzooxazol-5-yl)-7-methyl-7-propyl-6,7-dihydro-5H-pyrrolo[3,2-d]pyrimidin-4-ylamine;
5-(2-Amino-benzooxazol-5-yl)-7,7-diethyl-6-methyl-6,7-dihydro-5H-pyrrolo[3,2-d]pyrimidin-4-ylamine;
4-Amino-5-(2-amino-benzooxazol-5-yl)-7,7-dimethyl-5,7-dihydro-pyrrolo[3,2-d]pyrimidin-6-one;
1-Acetyl-4'-amino-5'-(2-aminobenzo[d]oxazol-5-yl)spiro[azetidine-3,7'-pyrrolo[3,2-d]pyrimidin]-6'(5'H)-one;
Tert-butyl-4'-amino-5'-(2-aminobenzo[d]oxazol-5-yl)-6'-oxo-5',6'-dihydrospiro[azetidine-3,7'-pyrrolo[3,2-d]pyrimidine]-1-carboxylate; or
Tert-butyl-4'-amino-5'-(2-aminobenzo[d]oxazol-5-yl)-5',6'-dihydrospiro[azetidine-3,7'-pyrrolo[3,2-d]pyrimidine]-1-carboxylate;
or a pharmaceutically acceptable salt thereof.

9. The composition according to claim 4, further comprising at least one other active ingredient selected from the group consisting of betamethasone dipropionate glycol, clobetasol 17-propionate, halobetasol propionate, amcinonide, desoximetasone, diflucortolone valerate, fluocinonide, halcinonide, momethasone furoate, triamcinolone acetonide, betamethasone valerate, clobetasone 17-butyrate, desonide, hydrocortisone 17-valerate, prednicarbate, hydrocortisone, hydrocortisone acetate, calcipotriol, calcitriol, adapalene, benzoyl peroxide, clindamycin and erythromycin.

10. The compound according to claim 1, which is:

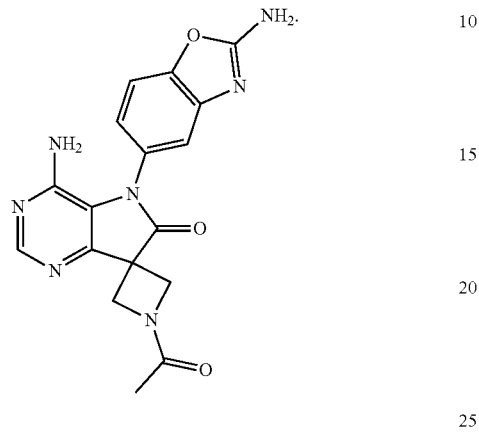

* * * * *